US011668694B2

(12) United States Patent
Lee et al.

(10) Patent No.: US 11,668,694 B2
(45) Date of Patent: *Jun. 6, 2023

(54) LEATHER INSPECTION SYSTEM

(71) Applicant: NIKE, Inc., Beaverton, OR (US)

(72) Inventors: Ming-Ji Lee, Douliou (TW); Chin-Yi Lin, Douliou (TW); Chun-Yen Tseng, Douliou (TW)

(73) Assignee: NIKE, Inc., Beaverton, OR (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/205,868

(22) Filed: Mar. 18, 2021

(65) Prior Publication Data

US 2021/0208126 A1 Jul. 8, 2021

Related U.S. Application Data

(63) Continuation of application No. 16/418,774, filed on May 21, 2019, now Pat. No. 10,955,403.

(60) Provisional application No. 62/674,730, filed on May 22, 2018.

(51) Int. Cl.
G01N 21/88 (2006.01)
G06T 7/00 (2017.01)
(Continued)

(52) U.S. Cl.
CPC ....... G01N 33/447 (2013.01); G01N 21/8806 (2013.01); G06T 7/0004 (2013.01);
(Continued)

(58) Field of Classification Search
CPC ........... G06T 7/0004; G06T 7/40; G06T 7/70; G06T 2207/30124; C14B 17/005;
(Continued)

(56) References Cited

U.S. PATENT DOCUMENTS

| 5,258,917 A | 11/1993 | Bruder et al. |
| 6,157,730 A | 12/2000 | Roever et al. |
| 10,955,403 B2 * | 3/2021 | Lee et al. ............. G01N 33/447 |

FOREIGN PATENT DOCUMENTS

| CN | 1786689 A | 6/2006 |
| CN | 1789990 A | 6/2006 |

(Continued)

OTHER PUBLICATIONS

Office Action received for European Patent Application No. 19730045.2, dated Oct. 28, 2022, 5 pages.

Primary Examiner — Andrew W Johns
(74) Attorney, Agent, or Firm — Shook, Hardy & Bacon L.L.P.

(57) ABSTRACT

A leather inspection apparatus is provided for detecting inconsistencies on both upper and lower surfaces of a hide. It includes a first camera assembly movably coupled to a support frame and capable of movement along the upper surface of the hide and a second camera assembly movably coupled to the support frame and capable of movement along the lower surface of the hide. A computing device is coupled to the first camera assembly and the second camera assembly, such that the first camera assembly detects the locations of inconsistencies in the upper surface of the hide and the second camera assembly detects the locations of inconsistencies in the lower surface of the hide. The computing device digitally stores the locations of the inconsistencies of the upper surface of the hide and the locations of the inconsistencies of the lower surface of the hide.

20 Claims, 15 Drawing Sheets

(51) Int. Cl.
*G01N 33/44* (2006.01)
*G01N 21/17* (2006.01)

(52) U.S. Cl.
CPC . *G01N 2021/177* (2013.01); *G01N 2201/102* (2013.01); *G06T 2207/30124* (2013.01)

(58) Field of Classification Search
CPC .. C14B 17/14; D06H 3/08; G01N 2021/0106; G01N 2021/0181; G01N 2021/177; G01N 21/86; G01N 2021/8609; G01N 21/88; G01N 21/8806; G01N 2021/8812; G01N 2021/8841; G01N 21/8851; G01N 2021/8887; G01N 21/89; G01N 21/8901; G01N 21/8914; G01N 21/8915; G01N 33/447; G01N 2201/102; G01N 2201/104
See application file for complete search history.

(56) References Cited

FOREIGN PATENT DOCUMENTS

| | | |
|---|---|---|
| CN | 102725627 A | 10/2012 |
| CN | 104766314 A | 7/2015 |
| CN | 105164281 A | 12/2015 |
| CN | 105301009 A | 2/2016 |
| CN | 205374331 U | 7/2016 |
| CN | 107238606 A | 10/2017 |
| CN | 107462520 A | 12/2017 |
| CN | 108037138 A | 5/2018 |
| DE | 4216469 A1 | 11/1993 |
| DE | 10207574 A1 | 9/2003 |
| DE | 102004015110 A1 | 10/2005 |
| EP | 2787485 A1 | 10/2014 |
| KR | 10-1226892 B1 | 2/2013 |
| KR | 10-2015-0102145 A | 9/2015 |

* cited by examiner

| PRIORITY | DEFECT CLASS | | ATTENDANCE FREQ. | AREA (MM X MM) |
|---|---|---|---|---|
| A | DIRT / HOLE / SCAR | | HIGH | 1.5 X 1.5 MM |
| | SCRATCH | | LOW | 10 X 1.5 MM |
| | DEEP WRINKLE | | HIGH | WIDE RANGE |
| B | SHALLOW DIRT / HOLE / SCAR | | MEDIUM | 2.5 X 2.5 MM |
| | BLOOD VESSEL (SHALLOW WRINKLE) | | UNCERTAIN | WIDE RANGE |

*FIG. 14.*

LEATHER INSPECTION SYSTEM

CROSS-REFERENCE TO RELATED APPLICATIONS

This application is a continuation application of pending U.S. application Ser. No. 16/418,774, entitled, "Leather Inspection System" filed May 21, 2019, which claims the benefit of U.S. Provisional Application No. 62/674,730, entitled, "Leather Inspection System" filed May 22, 2018, which are hereby incorporated by reference in their entireties.

TECHNICAL FIELD

Aspects hereof relate to apparatuses, systems and methods for inspecting leather for defects. More particularly, aspects relate to apparatuses, systems and methods for automatically inspecting leather and indicating the location of inconsistencies on the surface of the leather.

BACKGROUND

In the manufacture of articles of clothing, for example, shoes, a leather hide is often uses as a component of the article, for instance a shoe upper. A leather hide oftentimes has a variety of inconsistencies (such as defects) on its upper and its lower surface. Such inconsistencies can include such items as a hole, a scar, a scratch, a wrinkle, a blood vessel, or even dirt. It is desirous to not have any of these inconsistencies present in the portion of the leather hide utilized in the final article, for instance in the upper of a shoe. Such inconsistencies present unsightly interruptions in the smoothness of the leather and decrease the overall appearance of the finished article.

BRIEF SUMMARY

Aspects hereof provide an apparatus for detecting inconsistencies on both the upper and the lower surfaces of a leather hide. The apparatus includes a frame capable of supporting the hide. The apparatus also includes a first camera assembly movably coupled to the frame and capable of movement along the upper surface of the hide and a second camera assembly movably coupled to the frame and capable of movement along the lower surface of the hide. A computing device is operatively coupled to the first camera assembly and the second camera assembly so that the first camera assembly detects the locations of inconsistencies in the upper surface of the hide and the second camera assembly detects the locations of inconsistencies in the lower surface of the hide. The computing device digitally stores the locations of the inconsistencies of the upper surface of the hide and the locations of the inconsistencies of the lower surface of the hide.

Another aspect hereof includes an apparatus for detecting inconsistencies on a surface of a leather hide including a frame capable of supporting the hide. A camera assembly is movably coupled to the frame and capable of movement along a surface of the hide. The camera assembly includes a first camera and a second camera operatively coupled to a computing device. The camera assembly detects the locations of inconsistencies in the surface of the hide and the computing device digitally stores the locations of the inconsistencies of the surface of the hide. The first camera detects inconsistencies based on direct lighting and the second camera detects inconsistencies based on indirect lighting.

A further aspect includes a method for detecting inconsistencies on both upper and lower surfaces of a leather hide including the scanning of the upper surface of the hide to detect the locations of inconsistencies in the upper surface of the hide and the scanning of the lower surface of the hide to detect the locations of inconsistencies in the lower surface of the hide. The method also includes digitally storing the locations of the inconsistencies of the upper surface of the hide and the locations of the inconsistencies of the lower surface of the hide.

DESCRIPTION OF THE DRAWINGS

The present invention is described in detail herein with reference to the attached drawing figures, wherein:

FIG. 14 depicts a table showing the various types of inconsistencies (such as defects), their frequency, size, priority and way of marking;

DETAILED DESCRIPTION

Figure 1:
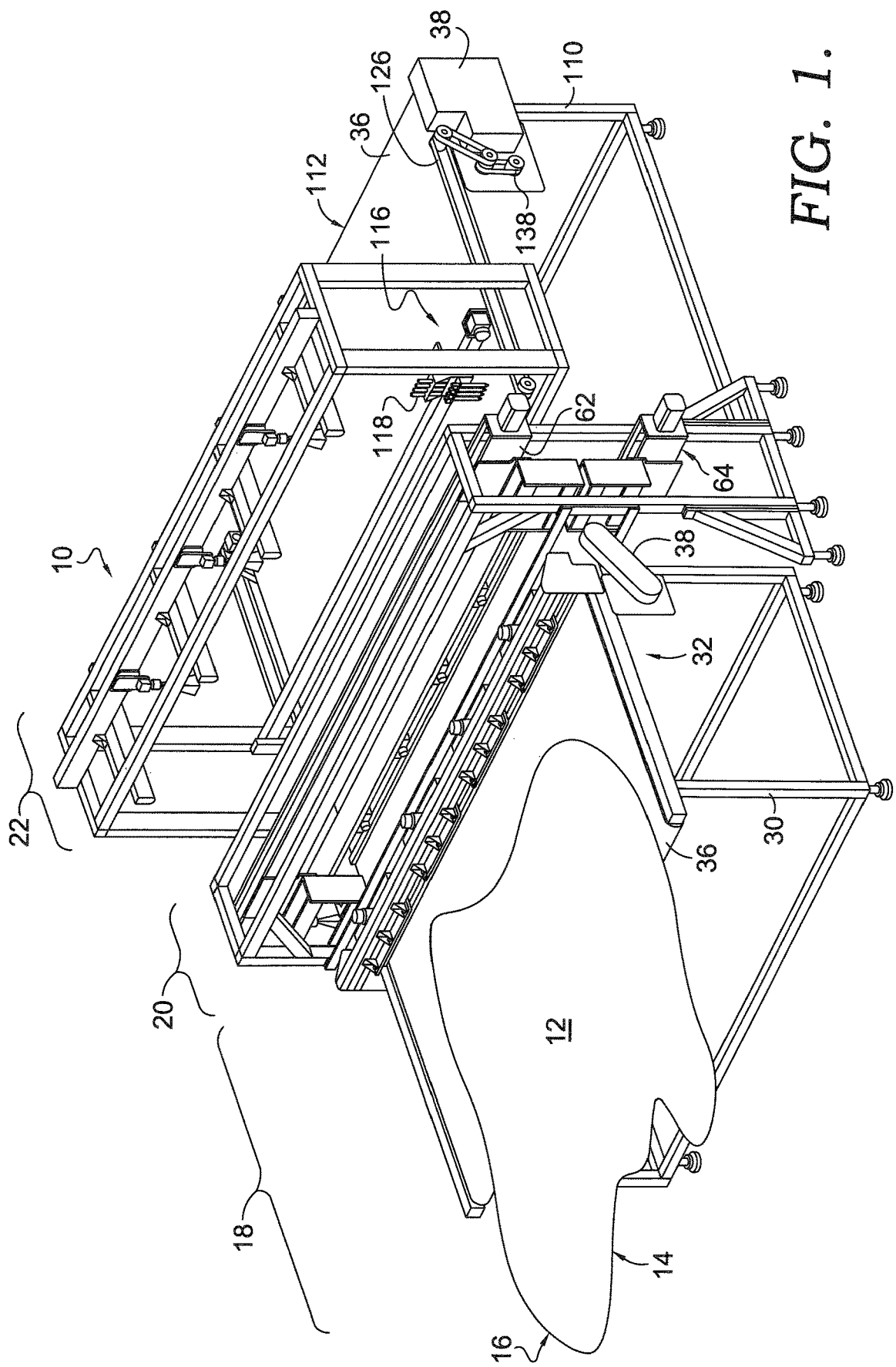
FIG. 1 depicts a top perspective view of a system for inspecting a leather hide, in accordance with exemplary aspects hereof.

Articles of clothing and accessories, such as jackets, shoes and purses, are often made of leather. Leather is typically provided to the article manufacturer from a tannery in the form of a hide which is an irregular-shaped planer item from which the article or a portion thereof is cut out. For instance, in the manufacturing of shoes, the upper of the shoe is often made partially of or solely of leather. Whatever the article, such as a shoe, that is manufactured, it is desirous to have a smooth surface on both the inner and outer surfaces of the article, the outer surface to ensure a superior appearance and the inner surface to insure comfort for the wearer. Additionally, if the interior surface of the article, for instance a shoe, is visible to a wearer, unseemly inconsistences (such as defects) are to be avoided. Because the hide is made from the skin of an animal, typically a cow, there are oftentimes many inconsistencies (such as defects) in the hide. These defects could include, for instance, but not limited to, holes, scars, scratches, insect bites, wrinkles, blood vessels or even dirt. When cutting out the portions of the hide to use in the article, it is desirous to ensure that none of these defects exist on either the outer surface of the article or the inner surface of the article. Therefore, it is desirous to have a clear indication of where the defects are on both surfaces of the hide so that an appropriate cutting operation can be performed while only having visual access to one of the surfaces.

Aspects hereof provide an apparatus for detecting inconsistencies on both the upper and lower surfaces of a leather hide. The apparatus includes a frame capable of supporting the hide. The apparatus also includes a first camera assembly movably coupled to the frame and capable of movement along the upper surface of the hide and a second camera assembly movably coupled to the frame and capable of movement along the lower surface of the hide. A computing device is operatively coupled to the first camera assembly and the second camera assembly so that the first camera assembly detects the locations of inconsistencies in the upper surface of the hide and the second camera assembly detects the locations of inconsistencies in the lower surface of the hide. The computing device digitally stores the locations of the inconsistencies of the upper surface of the hide and the locations of the inconsistencies of the lower surface of the hide.

Another aspect hereof includes an apparatus for detecting inconsistencies on a surface of a leather hide including a frame capable of supporting the hide. A camera assembly is movably coupled to the frame and capable of movement along a surface of the hide. The camera assembly includes a first camera and a second camera operatively coupled to a computing device. The camera assembly detects the locations of inconsistencies in the surface of the hide and the computing device digitally stores the locations of the inconsistencies of the surface of the hide. The first camera detects inconsistencies based on direct lighting and the second camera detects inconsistencies based on indirect lighting.

A further aspect includes a method for detecting inconsistencies on both upper and lower surfaces of a leather hide including the scanning of the upper surface of the hide to detect the locations of inconsistencies in the upper surface of the hide and the scanning of the lower surface of the hide to detect the locations of inconsistencies in the lower surface of the hide. The method also includes digitally storing the locations of the inconsistencies of the upper surface of the hide and the locations of the inconsistencies of the lower surface of the hide.

Figure 2:
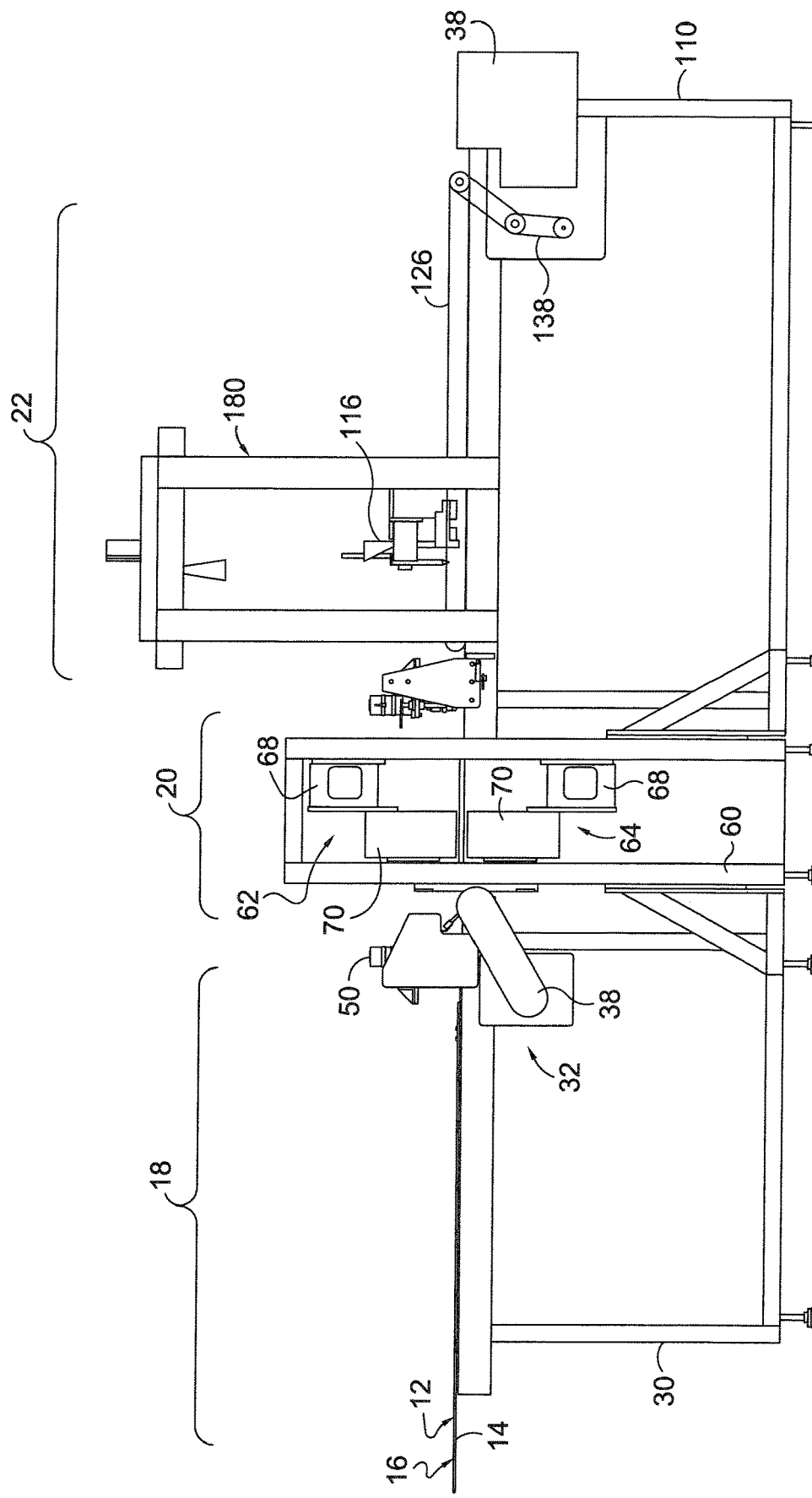
FIG. 2 depicts a side elevation view of the system in FIG. 1, in accordance with exemplary aspects hereof.
Figure 3:
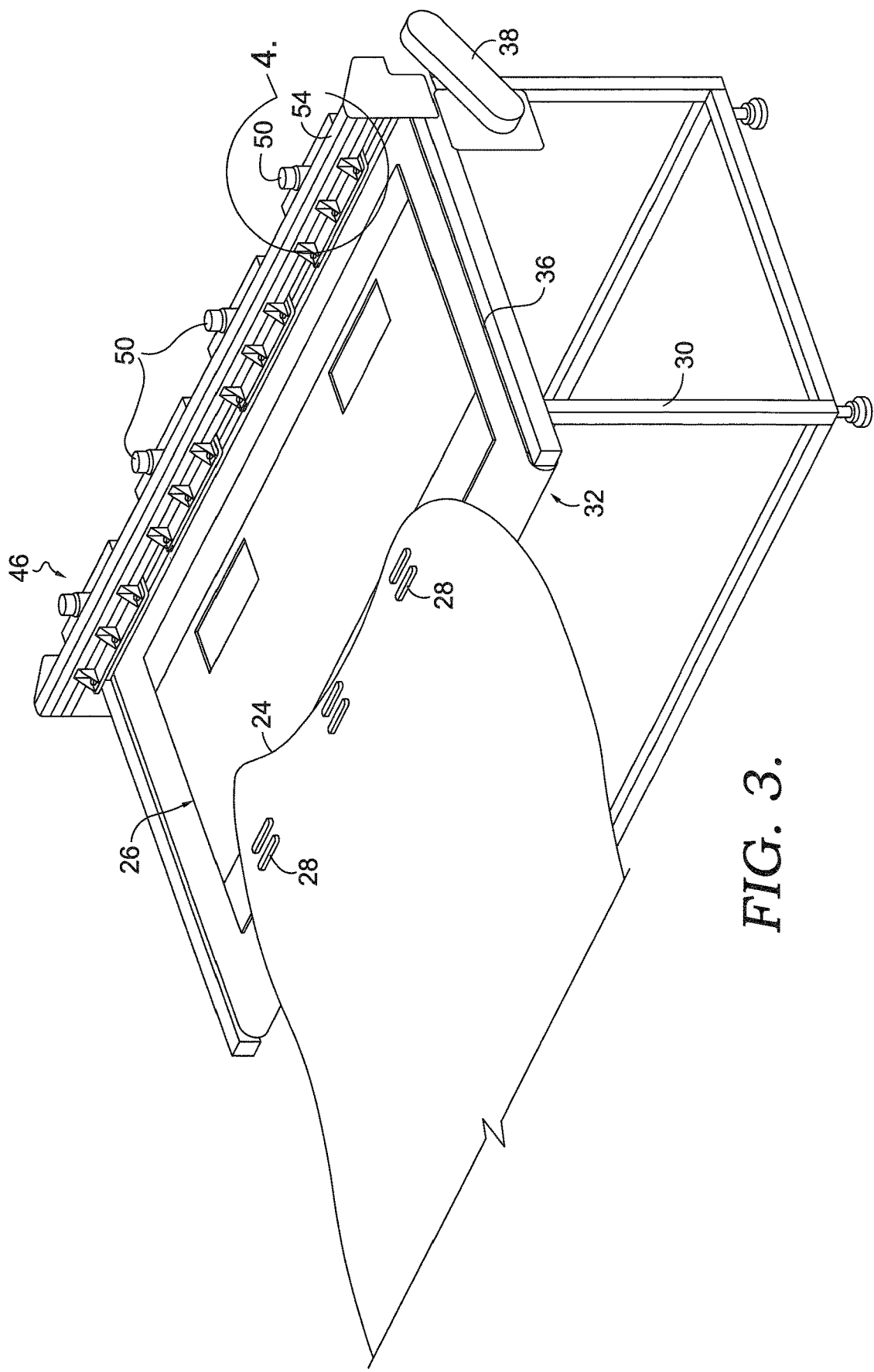
FIG. 3 depicts a top perspective view of a loading cell of the system of FIG. 1, in accordance with exemplary aspects hereof.
Figure 4:
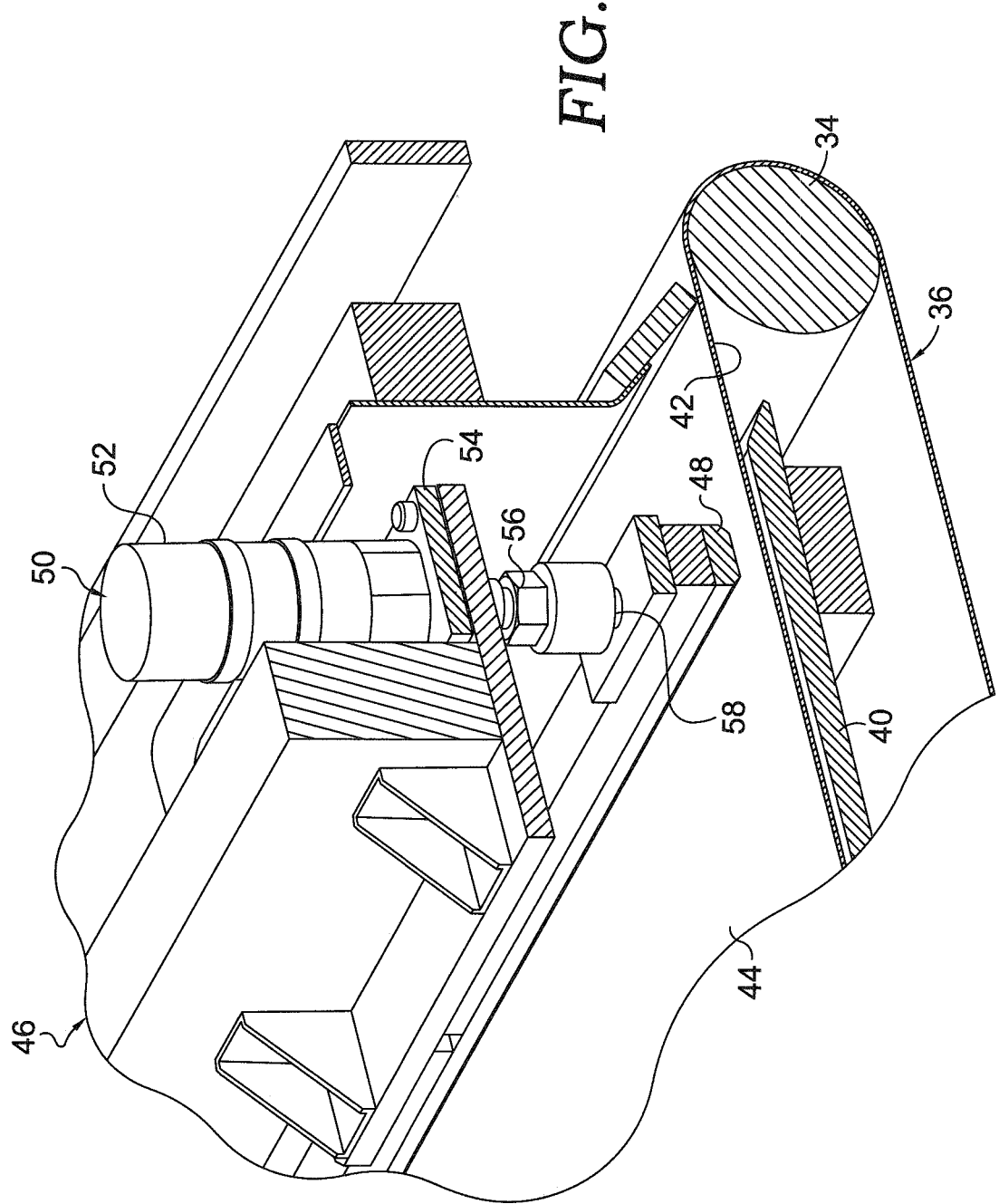
FIG. 4 depicts an enlarged top perspective cross section view of the area designated by the numeral 4 in FIG. 3, in accordance with exemplary aspects hereof.
Figure 5:
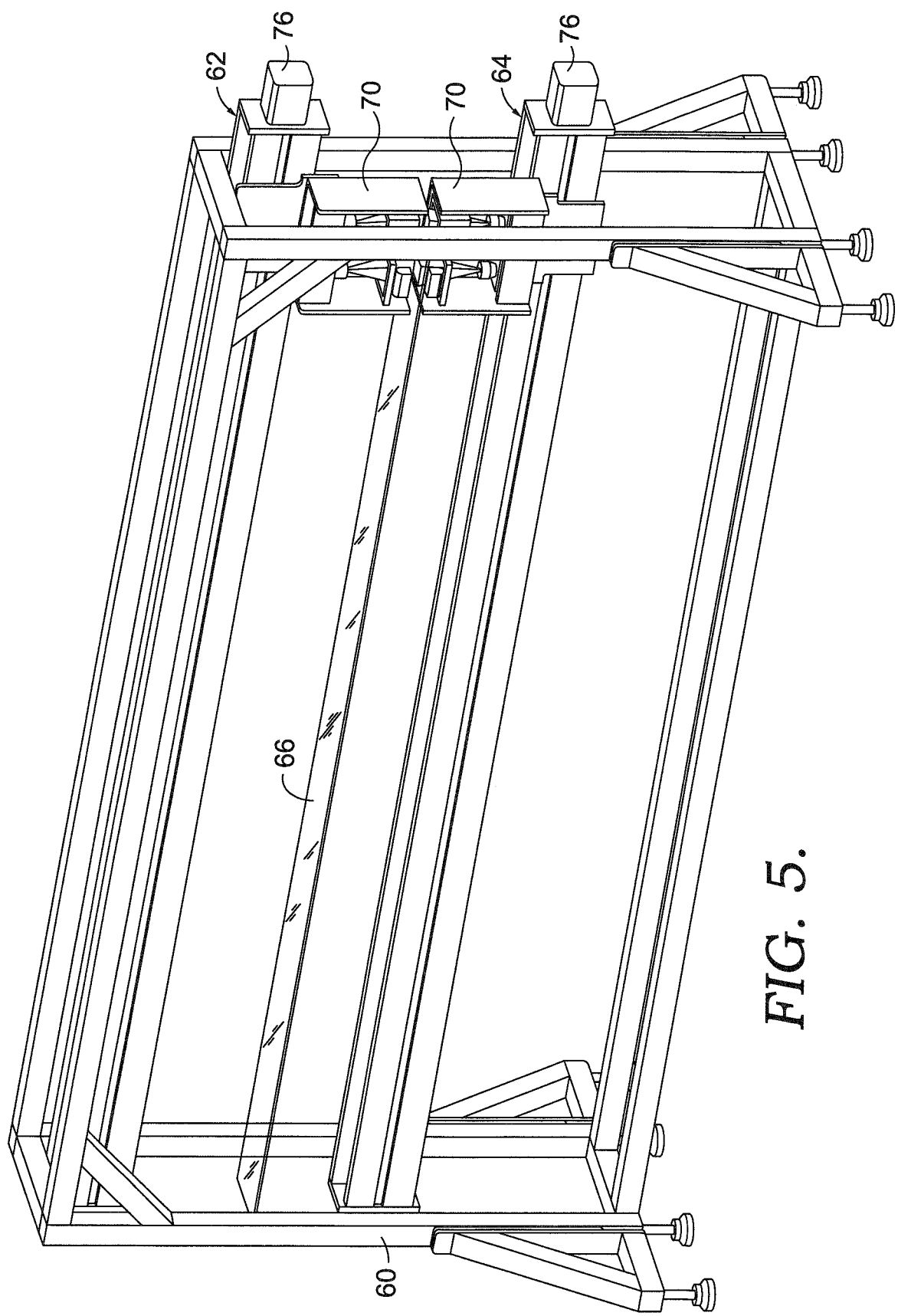
FIG. 5 depicts a top perspective view of the scanning cell of the system of FIG. 1, in accordance with exemplary aspects hereof.
Figure 6:
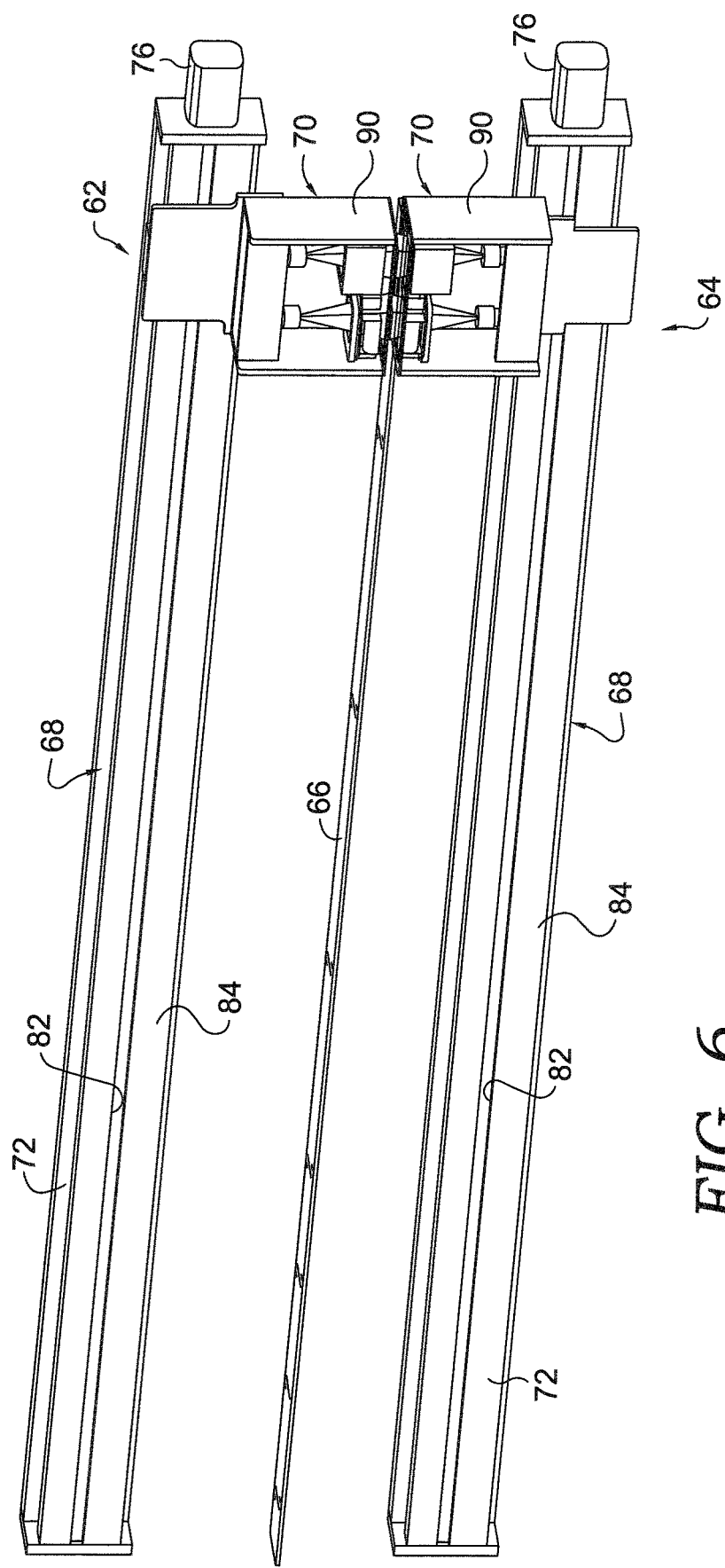
FIG. 6 depicts a front perspective view of the camera assemblies and drive mechanisms of the scanning cell of FIG. 5, in accordance with exemplary aspects hereof.

Referring to FIGS. 1 and 2, a leather inspection system 10 for detecting inconsistencies in both an upper surface 12 and a lower surface 14 of a hide 16 is depicted. The hide 16 is typically made of the tanned and treated skin of an animal, such as a cow. The hide 16 is also typically planer and can have a multitude of irregular shapes depending on a variety of processing techniques. The hide 16 may have inconsistencies in both its upper surface 12 and its lower surface 14. One example of inconsistencies may be defects, for instance, but limited to holes, scars, scratches, insect bites, wrinkles, blood vessels or even dirt.

The inspection system 10 includes a loading cell 18, a scanning cell 20, and a marking cell 22. The loading cell 18 serves to transport, load and hold the hide 16 for the scanning cell 20. The scanning cell 20 performs the scanning of the upper surface 12 and the lower surface 14 of the hide 16 to automatically detect any inconsistencies in the surfaces 12 and 14. The locations of inconsistencies of both surfaces 12 and 14 are stored in a suitable computing device. The marking cell 22 utilizes the stored locations of the inconsistencies of both surfaces 12 and 14 to make a physical indication of such locations on the upper surface 12 of the hide 16. Thus, a worker will have a physical indication on the upper surface 12 of both the inconsistencies in the upper surface 12 and the lower surface 14. The worker can utilize the physical indications of the inconsistencies to cut out a suitable component of an article of manufacture, for instance, but not limited to a shoe upper. It is also contemplated and within the scope of aspects hereof that the stored inconsistencies of both surface 12 and 14 in the computing device may be utilized in an automated cutting operation without any actual physical marking on the upper surface 12.

Referring to FIGS. 1-4, the loading cell 18 will be described. First, in order to easily have the hide 16 move through the system 10, it was found to be desirous to attach a leading portion 24 of the hide 16 to a planer loading jig 26. The loading jig 26 can be a rectangular sheet of plastic or metal and can have a variety of different attachment members 28 to secure the leading portion 24 to the jig 26. Attachment members 28 can pass through the hide 16 in a cutting type manner or may be less intrusive by for instance utilizing magnetic forces.

The loading cell 18 has a frame 30 that supports a loading conveyor mechanism 32 that is used to pass the hide 16 to the scanning cell 20. The conveyor mechanism 32 includes a pair of rollers 34 supporting a belt 36. A first of rollers 36 is driven by a suitable powered belt drive 38. The belt drive 38 can be powered in any suitable fashion, by for instance, but not limited to, an electric or pneumatic motor. The frame 30 also has a horizontal support plate 40 for supporting a lower surface 42 of the belt 36. An upper surface 44 of belt 36 engages the lower surface 14 of the hide 16. Therefore, as the belt 36 is powered by the belt drive 38, the engagement between the belt upper surface 44 and the hide lower surface 14 is what moves the hide 16 towards the scanning cell 20. Additionally, the loading jig 26 also engages the belt upper surface 44 and provides additional leading engagement towards the scanning cell 20. Thus, the loading cell 18 provides structure and mechanisms to move hide 16 and the attached loading jig 26 into the scanning cell 20.

The loading cell 18 further has a clamp mechanism 46 for periodically clamping the hide 16 between a clamping plate 48 of the clamp mechanism 46 and the belt upper surface 44. This clamping action takes place during the scanning of a portion of the hide 16 that is exposed to the scanning cell 20. More specifically, the conveyor mechanism 32 is actuated to move a portion of the hide 16 into the scanning cell 20. Once an appropriate portion of the hide 16 is in the scanning cell 20, the conveyor mechanism 32 is deactivated and the clamping mechanism 46 is actuated to secure a portion of the hide 16 adjacent the scanning cell 20 entrance to secure the hide 16 during scanning. The clamping plate 48 is movably coupled to a plurality of actuators 50. The actuators 50 can be of any suitable type for instance pneumatic or hydraulic cylinders or electrical solenoids. A cylinder 52 of each actuator 50 is secured to a mount beam 54 that is suspended above the conveyor mechanism 32 by the frame 30. A piston 56 of the each actuator 50 extends through an aperture (not shown) in beam 54 and is secured at a lower end 58 to the clamp plate 48. Thus, as the actuators 50 are activated in such a way as to extend pistons 56, the clamp plate 48 will engage the hide upper surface 12 so as to pinch or clamp the hide 16 between the clamp plate 48 and the belt upper surface 44. The conveyor mechanism 32 and the clamp mechanism 46 are automatically actuated by a computing device to act in unison with the scanning cell 20 and the marking cell 22 as will be further described herein.

Referring to FIGS. 1, 2, and 5-9, the scanning cell 20 will be described. The scanning cell 20 has a support frame 60 for supporting an upper transverse scanning mechanism 62 and a lower transverse scanning mechanism 64. The upper scanning mechanism 62 is used to automatically inspect the hide upper surface 12 for inconsistencies (such as defects) and the lower scanning mechanism 64 is used to automatically inspect the hide lower surface 14 for inconsistencies. The upper scanning mechanism 62 and the lower scanning mechanism 64 can be actuated, such that when the upper scanning mechanism 62 is scanning a portion of the hide upper surface 12, the lower scanning mechanism 64 is simultaneously scanning a portion of the hide lower surface 14 that is directly below the portion being scanned on the hide upper surface 12. As will be further described herein, the synchronization between the upper scanning mechanism 62 and the lower scanning mechanism 64 is accomplished by triggering the image scanning based upon target servo encoder values for the upper scanning mechanism 62 and the lower scanning mechanism 64. The support frame 60 also supports an elongated rectangular transparent plate 66 which allows the scanning of both the hide upper surface 12 and the hide lower surface 14. More specifically, the transparent plate 66 supports and engages the hide lower surface 14 when a portion of the hide 16 is in the scanning cell 20. As described herein, the transparent plate 66 allows the scanning mechanism 64 to inspect the hide lower surface 14 because of its transparent nature. The plate 66 can be made of any suitable transparent material, for instance glass or plastic. The desirous aspect of plate 66 is the ability to have lower imaging devices have visual access to the hide lower surface 14.

Figure 8:
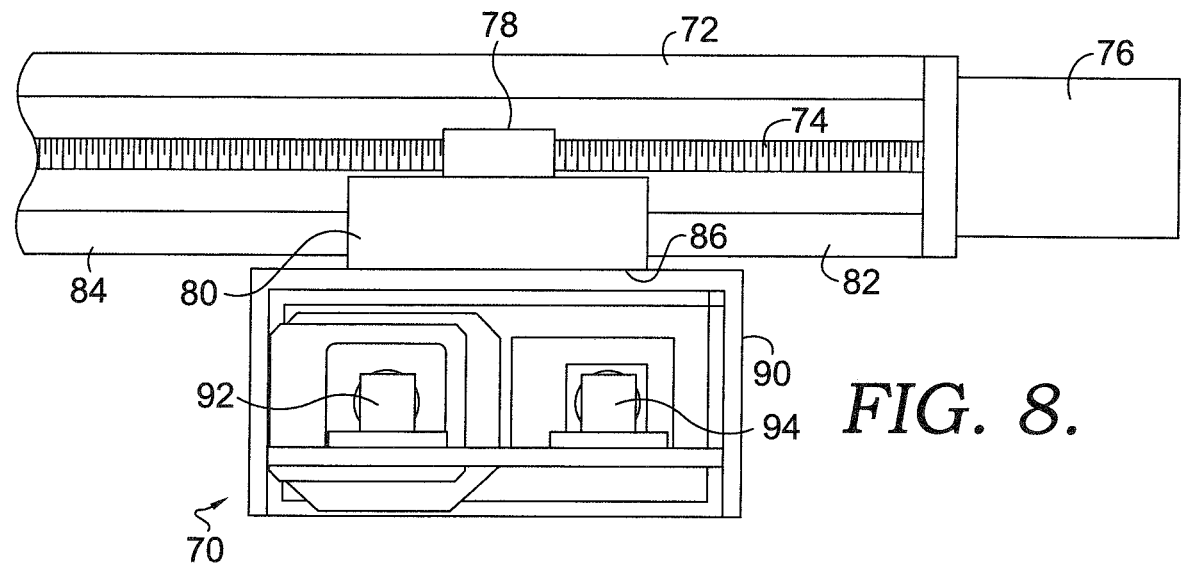
FIG. 8 depicts a top plan view of the upper camera assembly and drive mechanism in FIG. 7, parts broken away to reveal details of construction, in accordance with exemplary aspects hereof.

The scanning mechanisms 62 and 64 are identical in construction except that scanning mechanism 62 scans in a downward fashion and scanning mechanism 64 scans in an upward fashion. Each of scanning mechanisms 62 and 64 has a transverse screw actuator 68 for moving an imaging/camera assembly 70 back and forth across a transverse direction of the hide 16. Each screw actuator 68 includes a housing 72 that is supported by the frame 60. Referring to FIG. 8, each housing 72 includes a drive screw 74 which is rotated to effectuate the transverse motion of the image assembly 70. The drive screw 74 is power by a suitable rotary actuator 76. The rotary actuator 76 can be of any suitable type for instance a servomotor, a pneumatic motor, or an electric motor. Although as indicated, any suitable actuator capable of moving the image assembly 70 could be used. Each drive screw 74 is rotatably coupled to a movable carriage 78 via a male/female thread arrangement. More specifically, the drive screw 74 has a male thread arrangement and the carriage 78 has an aperture (not shown) with a female thread arrangement. Thus, as rotary actuator 76 is activated, drive screw 74 is rotated and, as a consequence, the carriage 78 is moved transversely along the drive screw 74. Connected to the carriage 78 is a connecting flange 80 for the image assembly 70. The connecting flange 80 extends through an elongated slot 82 formed on a front surface 84 of the housing 72. The connecting flange 80 moves with the carriage 78 as the carriage 78 is transported along the drive screw 74 by rotation of the drive screw 74. Thus, the flange 80 moves back and forth within the slot 82 as the carriage 78 moves transversely. The flange 80 is connected on a first end 86 to an upstanding connecting plate 88 of image assembly 70. The connecting plate 88 extends upwardly from a body 90 of the image assembly 70 in upper scanning mechanism 62. The connecting plate 88 extends downwardly from the body 90 of the image assembly 70 in the lower scanning mechanism 64. In this manner, as the respective carriage 78 moves along its respective drive screw 74 so does the respective image assembly 70 move transversely with respect to an inspected hide 16. This transverse movement of upper scanning mechanism 62 and lower scanning mechanism 64 results in the scanning of the hide upper surface 12 and the hide lower surface 14, respectively. The image assembly 70 of the upper scanning mechanism 62 can be synchronized with the image assembly 70 of the lower scanning mechanism 64, such that when the image assembly 70 of the upper scanning mechanism 62 is scanning a portion of the hide upper surface 12, the image assembly 70 of the lower scanning mechanism 64 is simultaneously scanning a portion of the hide lower surface 14 that is directly below the portion being scanned on the hide upper surface 12. The synchronization between the upper image assembly 70 and the lower image assembly 70 is accomplished by triggering the respective image assembly 70 based upon an identical series of target servo values for the respective transverse screw actuator 68. In this manner, the upper and lower image assemblies 70 are synchronized to take images of the upper hide surface 12 and the lower hide surface 14 at the same time bases upon an identical set of encoder values stored for each respective transverse screw actuator 68 and its associated rotary actuator 76. As is apparent, in this manner, the amount of time required to scan both the hide upper surface 12 and the hide lower surface 14 is significantly decreased. During the scanning operation, the image assemblies 70 can move from side to side along the entire length of scanning mechanisms 62 and 64. Thus, the image assemblies 70 in essence move from one side edge of the scanning cell 20 to the other side edge of the scanning cell 20. However, it may be advantages to increase efficiencies to only have the image assemblies 70 move back and forth over the hide 16 instead of moving along the entire length of the scanning mechanisms 62 and 64. In this manner, the image assemblies 70 would move back and forth from edge to edge of the hide 16 instead of moving back and forth from edge to edge of the scanning cell 20. This can increase the efficiency of the scanning operation by ensuring that the image assemblies 70 move between the edges of the hide 16 instead between the edges of the scanning cell 20 (where there may not be any portion of the hide 16 present). The camera 92 and/or the camera 94 of the image assemblies 70 (described in detail below) can be used to detect the edges of the hide 16. Each camera 92 and 94 can be coupled to a computing device, such that once an edge of the hide 16 is detected, the directions of the image assemblies 70 are reversed along their respective scanning mechanism 62 and 64. In addition to or in place of cameras 92 and/or 94, there may be others sensors placed on the scanning cell 20 to detect the edges of the hide 16.

Also, as is contemplated, the image assemblies 70 are not required to move in synchrony. The image assemblies can move in opposite directions or even in the same direction, but not vertically aligned. There may be situations where such a non-synchronous movement is advantages.

Figure 7:
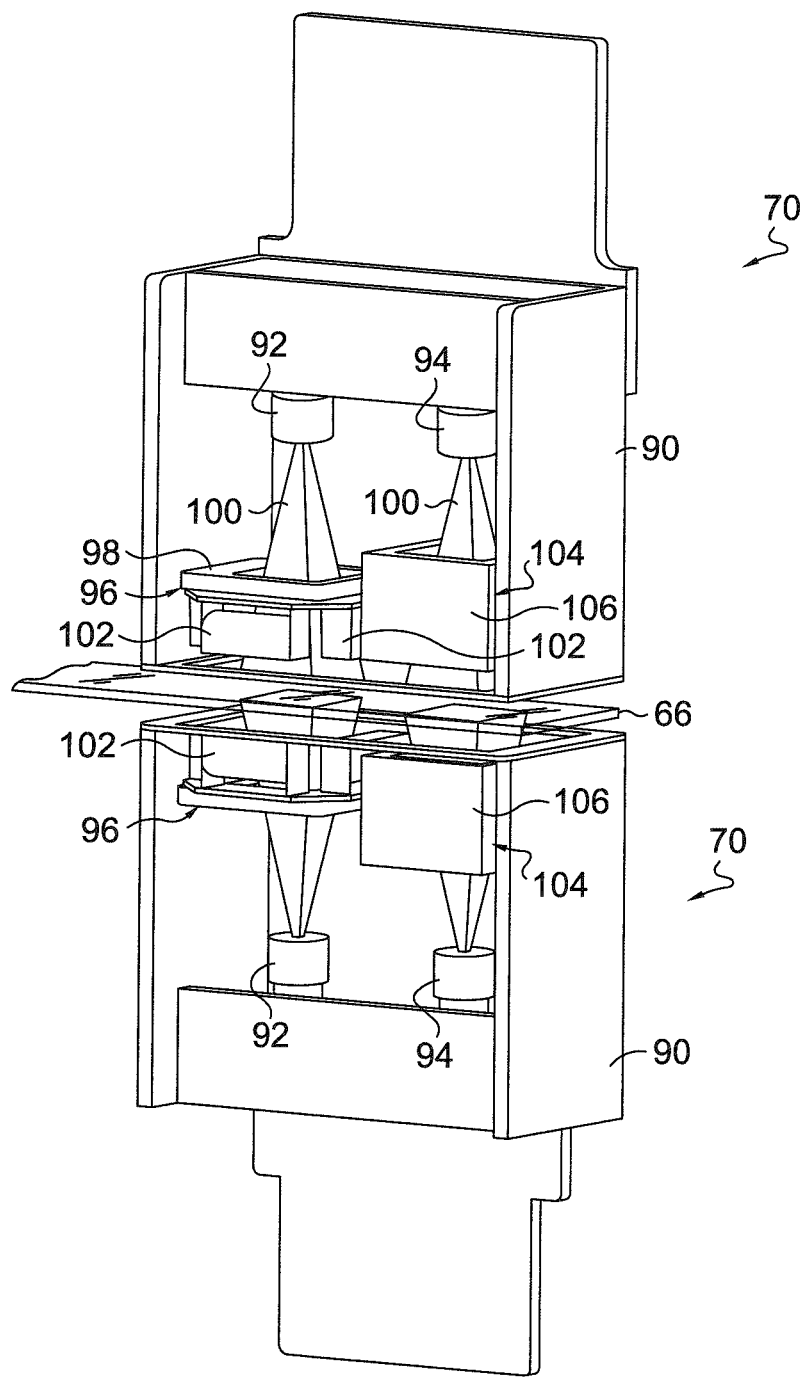
FIG. 7 depicts a top perspective view of the upper and lower camera assemblies of the scanning cell of FIG. 5, in accordance with exemplary aspects hereof.
Figure 9:
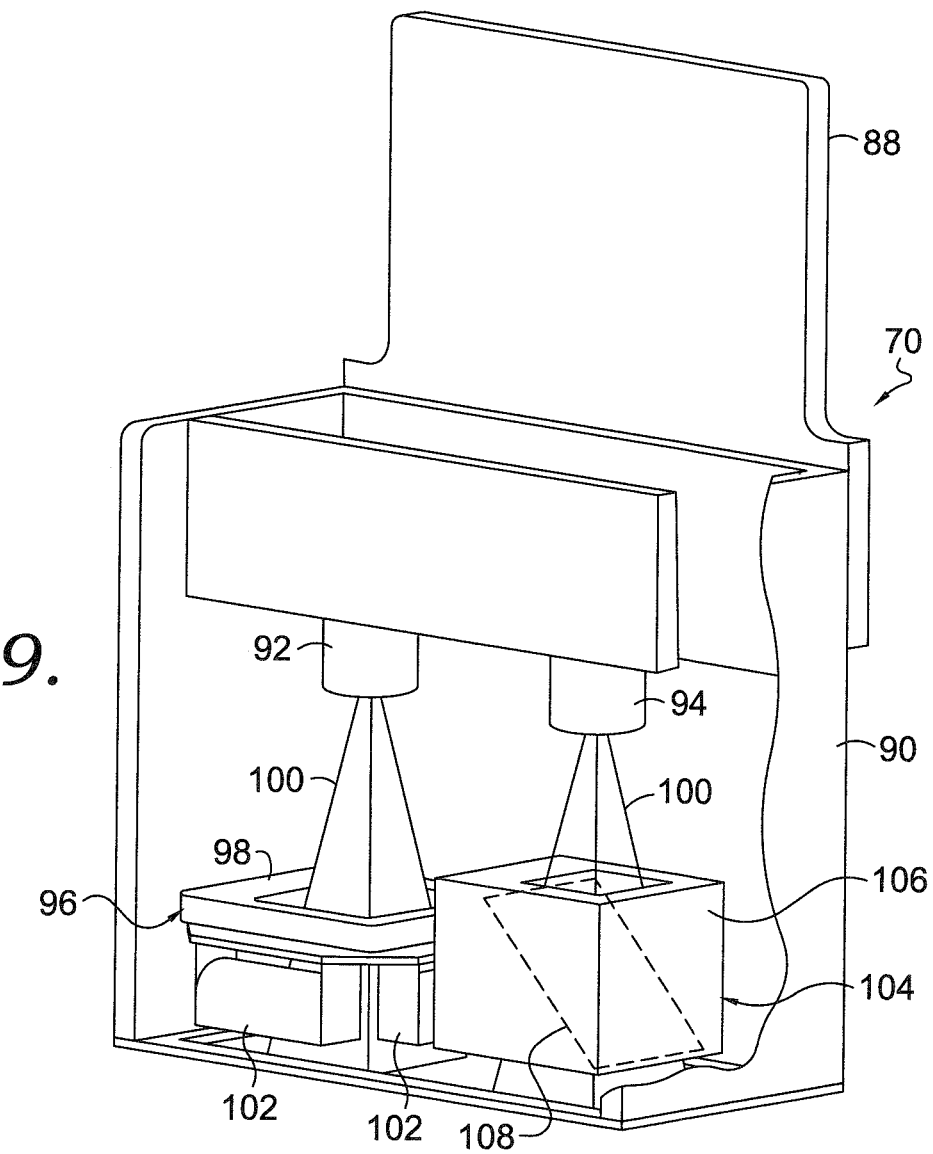
FIG. 9 depicts a top perspective view of the upper camera assembly in FIG. 7, parts broken away to reveal details of construction, in accordance with exemplary aspects hereof.

Referring to FIGS. 7-9, the body 90 of each image assembly 70 supports two cameras 92 and 94. The camera 92 scans and detects inconsistencies in in the surface of the hide 16 based upon indirect lighting and the camera 94 detects inconsistencies in the surface of the hide 16 based upon direct lighting. More specifically, it is contemplated that the camera 92 utilizing indirect lighting will detect eighty to ninety percent of the inconsistences in the hide upper surface 12 or the hide lower surface 14 depending on whether the image assembly 70 is associated with the upper scanning mechanism 62 or the lower scanning mechanism 64. Still further, the camera 94 utilizing direct lighting will capture the other ten percent or twenty percent of the inconsistencies in the hide upper surface 12 or the hide lower surface 14 depending on whether the image assembly 70 is associated with the upper scanning mechanism 62 or the lower scanning mechanism 64.

The indirect lighting of camera 92 is provided by an indirect lighting source 96. The indirect lighting source 96 includes a square shaped lighting structure 98 that surrounds a viewing field 100 of the indirect camera 92. The lighting structure 98 directs light through light bars 102 that is not aligned with the downward axial direction of the camera 92. An axial direction of a camera, such as the camera 92, is a central line (e.g., axis) extending from the camera in a direction of the field of view of that camera and perpendicular to the camera lens and/or centered in the field of view as captured from the camera. More specifically, the light bars 102 surround the viewing field 100 of the camera 92 and provides light that is at an angle to the axial direction of the camera 92. The light bars 102 of the indirect lighting structure 98 are supported by and connected to the image assembly body 90. Although one type of indirect lighting source 96 is described above, such description is in no way limiting and, it is in accordance with aspects hereof, that any type of structure that provides indirect light on the hide surface could be used.

The direct lighting of camera 94 is provided by direct lighting source 104. The direct lighting source 104 includes a light box 106 that surrounds the viewing field 100 of the camera 94. The light box 106 has a two way mirror 108 (shown in phantom) that allows the camera 94 to visually inspect the hide surfaces 12 or 14 depending on whether the camera 94 is part of the upper or lower scanning mechanism 62 or 64. The mirror 108 also reflects a light source (not shown) off its lower surface so that a light shines on surface 12 or 14 in a coaxial manner to the camera 94. The camera 94 can see through mirror 108 while the mirror 108 also reflects direct lighting on the surface 12 or 14. Although one type of direct lighting source 104 is described above, such description is in no way limiting and, it is in accordance with aspects hereof, that any type of structure that provides direct light on the hide surface could be used. In fact, it should be clear that either the indirect lighting source 96, the direct lighting source 104, or both lighting sources 96 and 104 could be eliminated in certain applications without departing from aspects hereof.

Any suitable machine vision camera can be utilized for cameras 92 and 94. One suitable camera could be of the nature of a charge—coupled device (CCD) image sensor. However any suitable technology could be utilized with the cameras 92 and 94 so long as the cameras 92 and 94 have the ability to detect inconsistencies in a hide surface. The camera 92 with its indirect light source 96 and the camera 94 with its direct coaxial light source 104 are operatively coupled to a computing device so that each of the cameras with their lighting sources can be selectively actuated. More specifically, it is contemplated, during a s scanning operation, to alternate actuation between the camera 92 with indirect light source 96 and camera 94 with direct light source 104 so that at any particular moment there is scanning taking place with only indirect light or direct light. This alternating arrangement prevents light pollution between the two different scanning operations, the indirect light scanning and the direct light scanning.

Although only one image assembly 70 is described for each of the upper scanning mechanism 62 and lower scanning mechanism 64, it is contemplated that there could be multiple image assemblies 70 associated with each of the scanning mechanism 62 and 64. In other words, multiple image assemblies 70 could be driven by the transverse actuator 68 so that different portions of the hide 16 could be scanned by different image assemblies 70.

Figure 10:
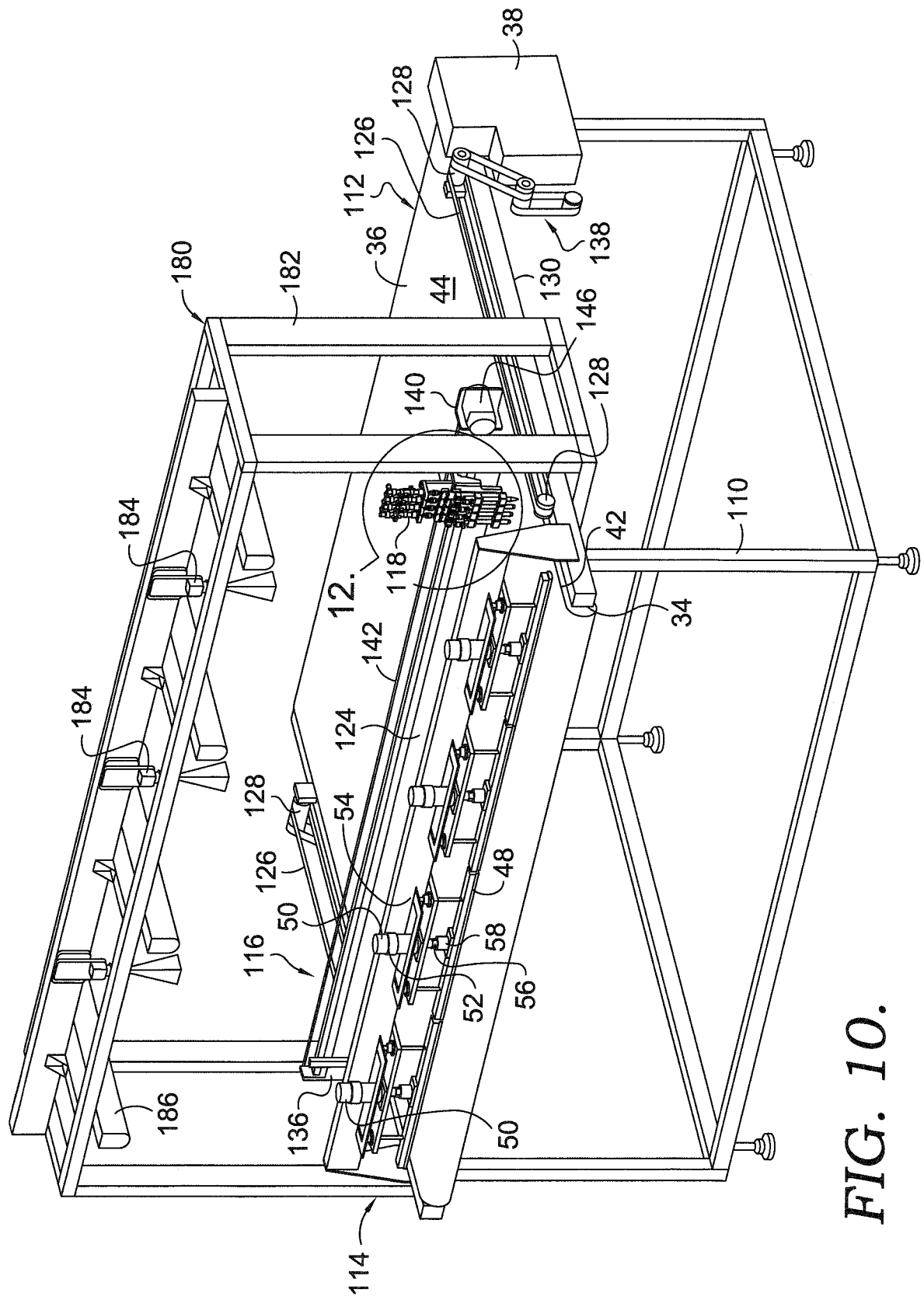
FIG. 10 depicts a top perspective view of the marking cell of the system of FIG. 1, in accordance with exemplary aspects hereof.
Figure 11:
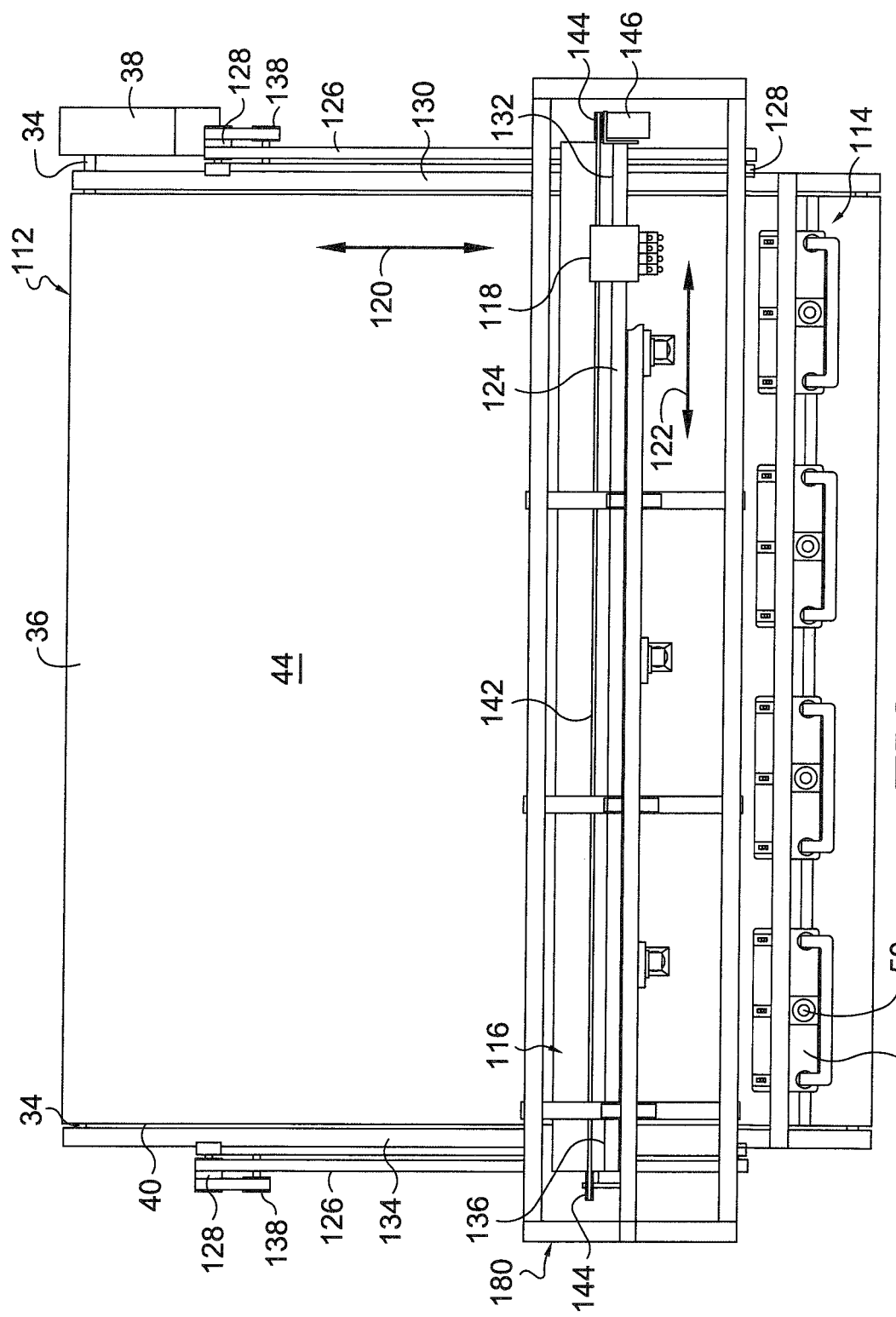
FIG. 11 depicts a top plan view of the loading cell in FIG. 10, in accordance with exemplary aspects hereof.
Figure 12:
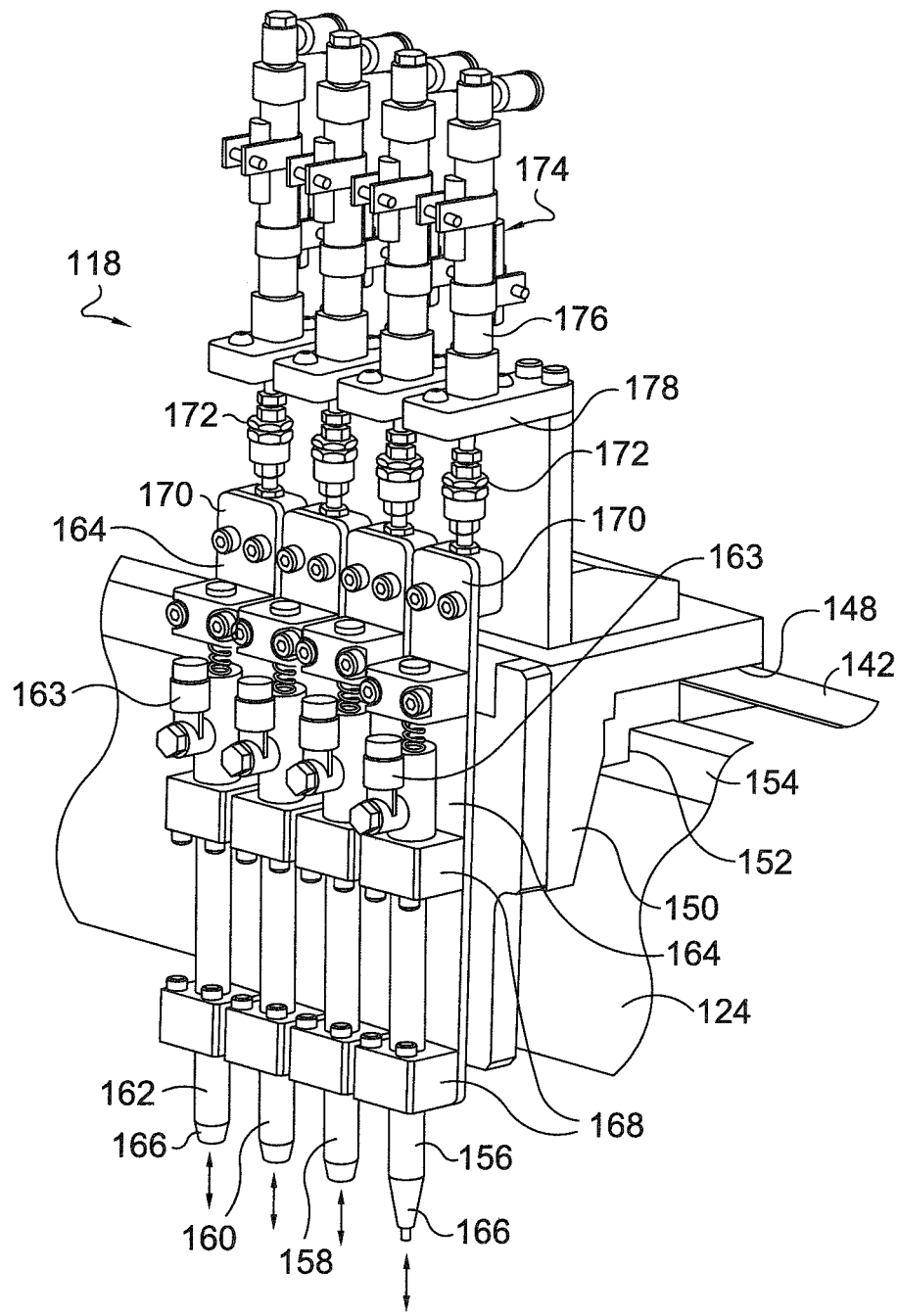
FIG. 12 depicts an enlarged top perspective view of the area designated by the numeral 12 in FIG. 10, in accordance with exemplary aspects hereof.

Referring to FIGS. 10-12, the marking cell 22 will be described. The marking cell 22 has a support frame 110 having a conveyor mechanism 112 that is similar to conveyor mechanism 32 of the loading cell 18. The difference between the two mechanisms is that mechanism 112 is used to unload the hide 16 from the scanning cell 20 instead loading the hide. The conveyor mechanisms 32 and 112 have the same or similar components and thus like numerals will be used to indicate like parts. The conveyor mechanism 112 includes a pair of rollers 34 supporting a belt 36. A first of rollers 36 is driven by a suitable powered belt drive 38. The belt drive 38 can be powered in any suitable fashion, by for instance, but not limited to, an electric or pneumatic motor. The frame 110 also has a horizontal support plate 40 for supporting a lower surface 42 of the belt 36. An upper surface 44 of belt 36 engages the lower surface 14 of the hide 16. Therefore, as the belt 36 is powered by the belt drive 38, the engagement between the belt upper surface 44 and the hide lower surface 14 is what moves the hide 16 away from the scanning cell 20. Additionally, the jig 26 also engages the belt upper surface 44 and provides additional engagement away from the scanning cell 20. Thus, the conveyor mechanism 112 moves the hide 16 and the attached loading jig 26 away from the scanning cell 20.

The marking cell 22 further has a clamp mechanism 114 that is similar or identical to clamp mechanism 46 of loading cell 18 and thus, like numerals will be used to designate like parts. The difference between the clamp mechanism 114 and the clamp mechanism 46 is that clamp mechanism 114 secures the hide 16 during scanning on the exiting side of the scanning cell 20 and the clamp mechanism 46 secures the hide 16 on the entry side of the scanning cell 20. The clamp mechanism 114 is used for periodically clamping the hide 16 between a clamping plate 48 of the clamp mechanism 114 and the belt upper surface 44. This clamping action takes place during the scanning of a portion of the hide 16 that is exposed to scanning cell 20. More specifically, the conveyor mechanism 112 is actuated to move a portion of the hide 16 away from the scanning cell 20. Once an unscanned portion of the hide 16 is in the scanning cell 20, the conveyor mechanism 112 is deactivated and the clamping mechanism 114 is actuated to secure a portion of the hide 16 adjacent the scanning cell 20 exit to secure the hide 16 during scanning. The clamping plate 48 is movably coupled to a plurality of actuators 50. The actuators 50 can be of any type for instance pneumatic or hydraulic cylinders or electrical solenoids. A cylinder 52 of each actuator 50 is secured to a mount beam 54 that is suspended above the conveyor mechanism 112 by the frame 110. A piston 56 of the each actuator 50 extends through an aperture (not shown) in beam 54 and is secured at a lower end 58 to the clamp plate 48. Thus, as the actuators 50 are activated in such a way as to extend pistons 56, the clamp plate 48 will engage the hide upper surface 12 so as to pinch or clamp the hide 16 between the clamp plate 48 and the belt upper surface 44. The conveyor mechanism 112 and the clamping mechanism 114 are automatically actuated by a computing device to act in unison with the scanning cell 20 and the loading cell 18 as will be further described herein.

The support frame 110 also supports a marking drive mechanism 116 that allows movement of a marking carriage 118 in two different directs 120 and 122 that are perpendicular to one another as shown in FIG. 11. More specifically, the marking drive mechanism 116 allows the positioning of the marking carriage 118 at any transverse or longitudinal position above the hide 16 after it has been scanned. Thus, once a portion of the hide 16 has been scanned, and that portion is within the marking cell 22, the marking drive mechanism 116 can be used to position the marking carriage 118 above the locations of the inconsistencies in the hide upper surface 12 and the hide lower surface 14 and thereafter effectuate a physical marking on the hide upper surface 12 at the locations of both the inconsistencies of the hide upper surface 12 and the hide lower surface 14.

The marking drive mechanism 116 includes a slide bar 124 that extends transversely across and is slidably coupled to the support 110. The slide bar is capable of back and forth movement in the direction 120. The slide bar 124 is selectively actuated to any location along direction 120 by a pair of drive belts 126 rotatably mounted to the frame 110 by rollers 128. More specifically, one drive belt 126 is located on one side 130 of the frame 110 and coupled to one end 132 of the slide bar 124. The other drive belt 126 is located on the other side 134 of the frame 110 and coupled to the other end 136 of the slide bar 124. Each of the belts 126 are powered by a suitable belt drive 138 mounted to the frame 110. The belt drives 138 are selectively actuated in unison so as to move belts 126 in unison. In this manner, movement of the slide bar 124 in the direction 120 is effectuated as directional force is transferred from the belts 126 to the ends 132 and 136 of the slide bar 124.

The marking carriage 118 is slidably coupled to the slide bar 124 so that the carriage 118 can move back and forth along the slide bar 124 in the transverse direction 122. Thus, the carriage 118 can be dispersed to any position along the slide bar 124. The carriage 118 is powered for movement along the slide bar 124 by the carriage drive mechanism 140 which is supported by and coupled to the slide bar 124. The carriage drive mechanism 140 includes a carriage belt 142 rotatably mounted on rollers 144 and driven by a rotary actuator 146. The rotary actuator 146 drives one of the rollers 144 such that the carriage belt 142 can be driven. The rotary actuator 146 can be selectively actuated to move the belt 142 in the direction 122. A mid portion of the belt 142 is coupled to the marking carriage 118 at a connection point 148 such that as the belt 142 moves back and forth in the direction 122 so does the marking carriage 118 move back and forth in direction 122. The rotary actuator 146 can be any suitable actuator capable of selective rotary motion, for instance an electric or pneumatic motor. The entire carriage drive mechanism 140 including the carriage belt 142, the rollers 144, and the rotary actuator 146 are mounted to move with the slide bar 124 as it moves in the direction 120. In this manner, the marking drive mechanism 116 is capable of being actuated to position the marking carriage at any position above a hide 16 along a coordinate system defined by the directions 120 and 122.

Referring to FIG. 12, the marking carriage 118 will be described. The marking carriage includes a body 150 that is slidably received on the slide bar 124 and operatively coupled to the carriage drive belt 142. The body 150 includes a slot 152 that slidably engages a rail 154 of the slide bar 124. It is this slidable engagement between the slot 152 and the rail 154 that allows the marking carriage 118 to move along the slide bar 124. The body 150 includes a plurality of marking pen tubes 156, 158, 160, and 162. Each of the tubes is configured to receive an appropriate pen that can have different attributes, such as color or texture. Each of the tubes 156, 158, 160, and 162 has an air pressure source 163 coupled thereto. The air pressure source 163 serves to selectively force the ink within a pen located in a respective tube downwardly towards the hide upper surface 12 to assist the marking action. The air pressure source 163 can be further used to perform any mechanical action required by a pen located in a respective tube, such as extending or retracing a marking tip. Each air pressure source 163 can be selectively and individually actuated at any appropriate time to effectuate or enhance the marking ability of a pen contained in one of the tubes 156, 158, 160, and 162. Each of the tubes (and the respective pen located therein) can be individually and selectively actuated (as indicated by the arrows in FIG. 12) to engage and mark the hide upper surface 12 at the locations of the inconsistencies of the hide upper surface 12 and the hide lower surface 14. The tubes 156, 158, 160 and 162 can contain a variety of pens of different types of colors or ink. For instance, the tube 156 can contain a silver marking pen. Still further, for example, the tube 158 can include a yellow pen, the tube 160 can include a red pen, and the tube 162 can include a blue pen. In this manner, for instance, a particular type of defect can be marked with a specific color, as will be more fully described herein. Each of the tubes 156, 158, 160, and 162 is mounted in a cartridge 164 that is slidably mounted to the carriage body 150 for selective actuation in an up and down manner that results in engagement and disengagement of the pen marking tips 166 of pens contained within the tubes 156, 158, 160, and 162 with the hide upper surface 12. The tubes 156, 158, 160, and 162 are mounted to their respective cartridge 164 by the brackets 168. The upper end 170 of each cartridge 164 is coupled to a piston 172 of a linear actuator 174. Each actuator 174 also has a cylinder 176 mounted to a support bracket 178 connected to and extending upwardly from the body 150. Each piston 172 extends through an aperture (not shown) in the support bracket 178. Each actuator 174 can be selectively actuated to extend the respective piston 172 resulting in the downward movement of the respective cartridge 164, and thus, resulting in the engagement of the respective pen contained within its respective tube with the hide upper surface 12 for marking. The actuators 174 can be of any suitable type for instance pneumatic, hydraulic, or electric.

As is apparent, the marking drive mechanism 116 allows the positioning of the marking carriage 118 at a wide range of positions above the hide upper surface 12. Still further, the actuation of the various tubes 156, 158, 160, and 162 on the marking carriage 118 allows for engagement of a marking tip 166 of one of the pens contained within one of the tubes. By controlling the drive mechanism 116 in both the direction 120 and the direction 122 while a marking tip 166 of any of the pens located in the tubes 156, 158, 160, and 162 is engaged with the hide upper surface 12, a variety of shapes and lines of all sizes and colors can be marked on the hide upper surface 12 to indicate the locations of inconsistencies in both the hide upper surface 12 and the hide lower surface 14. Examples of shapes, include, without limitation, circles, ovals, squares, rectangles, and/or triangles. Examples of lines, include, without limitation solid lines, dashed lines and/or wavy or curved lines. Thus, the location, size and type of inconsistency can be indicated on the hide upper surface 12 with a particular shape, color or line as drawn by the marking carriage 118 and the marking drive mechanism 116. As is apparent, the marking drive mechanism 116 and the marking carriage 118 operate independently of, but can also operate in conjunction with, the conveyor mechanism 112. The conveyor mechanism 112 can be actuated to reposition a portion of the hide 16 so that it is within operational range of the marking drive mechanism 116 and then the drive mechanism 116 can perform the drawing operation. The drawing operation of the drive mechanism 116 can also be actuated at the same time as the conveyor mechanism 112. As will be more fully describe, the conveyor mechanism 112, the marking drive mechanism 116 and the marking carriage 118 are all electronically coupled to and controlled by a suitable computing device.

The marking cell 22 also includes a calibration unit 180 for calibrating the location of the hide 16 on the support frame 110 to assist the marking drive mechanism 116 and the marking carriage 118 to locate the proper locations to physically mark the inconsistences on the hide upper surface 12. The unit 180 includes a frame 182 supporting a plurality of machine vision cameras 184 and light bars 186. The cameras 184 and the light bars 186 are electrically coupled to a suitable computing device so as to assist the correct positioning of the marking carriage 118 based upon the location of the hide 16 as it exits the scanning cell 18.

Figure 13:
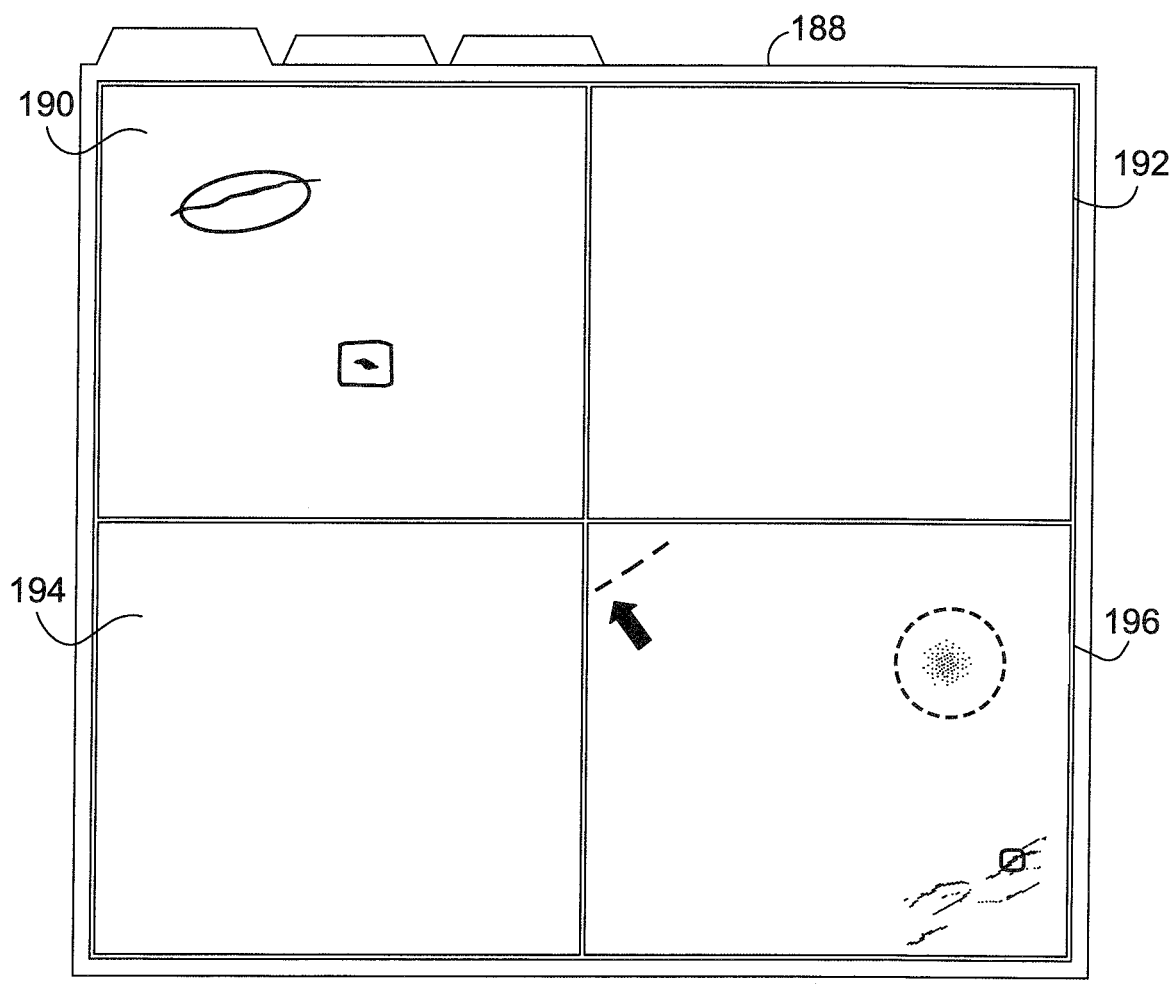
FIG. 13 depicts a computer monitor showing various inconsistencies as scanned by the camera assembly of FIG. 7, in accordance with exemplary aspects hereof.

Referring to FIG. 13, a window 188 on a computer monitor is depicted. The window 188 is divided into four sections 190, 192, 194, and 196. The first section 190 depicts what the upper indirect lighting camera 92 is seeing and the digital marking of the inconsistencies in the hide upper surface 12. The digital markings are shown as an oval to indicate one type of inconsistency and a square to indicate another type of inconsistency. These digital markings are rendered by a suitable computing device and exist in computer memory. The digital markings can be rendered into actual physical markings on the hide upper surface 12 by the marking drive mechanism 116 and the marking carriage 118. The digital markings can also be kept in computer memory and used in an automatic cutting operation, where it is not necessary to physically mark on the hide upper surface. The section 192 depicts what an upper direct lighting camera 94 is seeing. This section 192 is not picking up any defects so no digital markings are found in this section. The sections 190 and 192 can be for approximately the same portion of the hide upper surface 12 and demonstrates how an indirect lighting camera 92 may pick up defects that are not seen by the direct lighting camera 94. The section 194 depicts what the lower indirect lighting camera 92 is seeing. This section 194 is not picking up any defects so no digital markings are found in the section. The section 196 depicts what the lower direct lighting camera 94 is seeing and the digital markings of the inconsistencies in the hide lower surface 14. The digital markings are shown as a dashed line to indicate one type of inconsistency, a dashed circle to indicate another type of inconsistency, and a square to indicate further type of inconsistency. These digital markings are rendered by a suitable computing device and exist in computer memory. The digital markings can be rendered into actual physical markings on the hide upper surface 12 by the marking drive mechanism 116 and the marking carriage 118. The digital markings can also be kept in computer memory and used in an automatic cutting operation, where it is not necessity to physically mark on the hide upper surface. The sections 194 and 196 can be for approximately the same portion of the hide lower surface 14 and demonstrates how direct lighting camera 94 may pick up defects that are not seen by the indirect lighting camera 92.

FIG. 14 depicts a table 198 of potential inconsistencies in the form of defects and indicates the priority in detecting, the frequency in which they occur, and their approximate size. The table 198 also reflects how a particular defect may be digitally marked in computer memory or physically marked on the hide upper surface 12. For instance, a square 200 indicates dirt, a hole or a scare; an oval 202 indicates a scratch; a small square 204 indicates a deep wrinkle; a dashed circle 206 indicates shallow dirt, a hole or a scare; and a dashed line indicates a blood vessel or shallow wrinkle.

Figure 15:
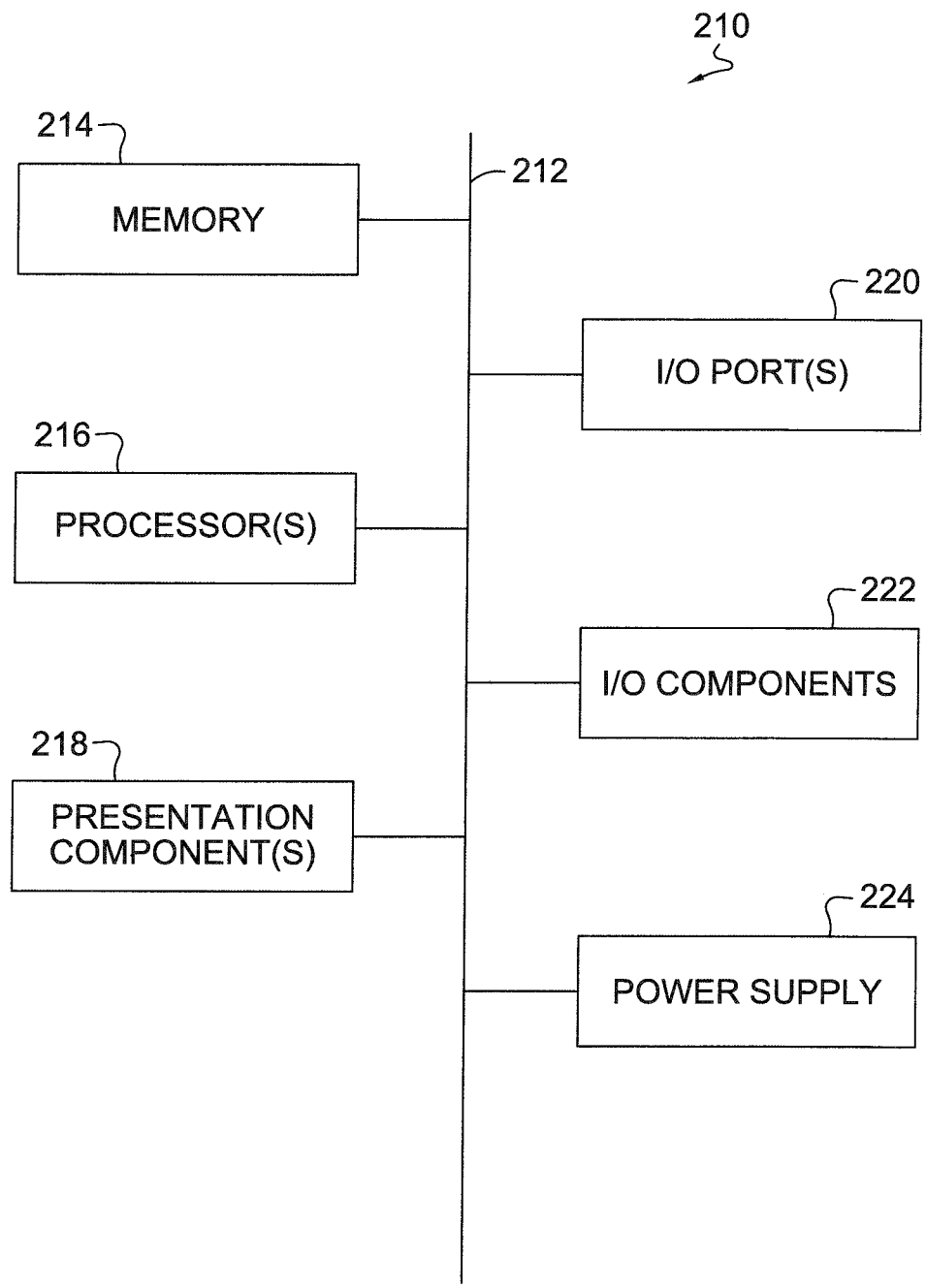
FIG. 15 depicts an exemplary computing operating environment, such as a programmable logic controller and/or a personal computer, for implementing aspects hereof.

FIG. 15 depicts an exemplary computing operating environment for implementing aspects hereof as shown and designated generally as computing system or device 210. For example, aspects provided herein contemplated using a computing device to control and synchronize all aspects the loading cell 18, the scanning cell 20, and the marking cell 22. More specifically the computing device 210 is electrically couple to and controls the conveyor mechanism 32, the clamp mechanism 46, the upper scanning mechanism 62 and its associated image assembly 70, the lower scanning mechanism 64 and its associated image assembly 70, the conveyor mechanism 112, the clamp mechanism 114, the marking drive mechanism 116, the marking carriage 118, and the calibration unit 180. The computing device 210 is further used to store the locations of the inconsistencies in both the hide upper surface 12 and the hide lower surface 14 and utilize those stored locations to physically mark all inconsistencies from both the hide upper surface 12 and the hide lower surface 14 on the hide upper surface. The computing device 210 is but one example of a suitable computing environment and is not intended to suggest any limitation as to the scope of use or functionality of the invention. Neither should the computing device 210 be interpreted as having any dependency or requirement relating to any one or combination of components illustrated.

Aspects herein may be described in the general context of computer code or machine-useable instructions, including computer-executable instructions such as program components, being executed by a computer or other machine, such as a programmable logic controller ("PLC"). Generally, program components, including routines, programs, objects, components, data structures, and the like, refer to code that performs particular tasks or implements particular abstract data types. Aspects hereof may be practiced in a variety of system configurations, including handheld devices, consumer electronics, general-purpose computers, personal computers, specialty computing devices, PLC, etc. Aspects hereof may also be practiced in distributed computing environments where tasks are performed by remote-processing devices that are linked through a communications network.

With continued reference to FIG. 15, computing device 210 includes a bus 212 that directly or indirectly couples the following devices: memory 214, one or more processors 216, one or more presentation components 218, input/output (I/O) ports 220, I/O components 222, and an illustrative power supply 224. Bus 212 represents what may be one or more busses (such as an address bus, data bus, or combination thereof). Although the various blocks of FIG. 15 are shown with lines for the sake of clarity, in reality, delineating various components is not so clear, and metaphorically, the lines would more accurately be grey and fuzzy. For example, one may consider a presentation component such as a display device to be an I/O component 222. Also, processors have memory. It is recognized that such is the nature of the art, and reiterated that the diagram of FIG. 15 is merely illustrative of an exemplary computing device that can be used in connection with one or more aspects hereof. Distinction is not made between such categories as "workstation," "server," "laptop," "handheld device," "tablet," "phone," "node," "PLC," etc., as all are contemplated within the scope of FIG. 15 and refer to "computer" or "computing device." In particular, aspects hereof are contemplated as being performed in whole or in part on one or more components of a distributed computing system. It is contemplated that a distributed computing system may be comprised of processors, networks, and memory that scale to handle as desired level of computing processes at a time. Therefore, it is contemplated that a computing device may also refer to the computing environment of a distributed computing system that dynamically changes with time and/or demand.

Computing device 210 typically includes a variety of computer-readable media. Computer-readable media can be any available media that can be accessed by computing device 210 and includes both volatile and nonvolatile media, removable and non-removable media. By way of example, and not limitation, computer-readable media may comprise computer-storage media and communication media. Computer-storage media includes both volatile and nonvolatile, removable and non-removable media implemented in any method or technology for storage of information such as computer-readable instructions, data structures, program modules or other data.

Computer-storage media includes RAM, ROM, EEPROM, flash memory or other memory technology, CD-ROM, digital versatile disks (DVD) or other optical disk storage, magnetic cassettes, magnetic tape, magnetic disk storage or other magnetic storage devices. Computer storage media does not comprise a propagated data signal.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 214 includes computer-storage media in the form of volatile and/or nonvolatile memory. The memory 214 may be removable, nonremovable, or a combination thereof. Exemplary memory includes non-transitory, solid-state memory, hard drives, optical-disc drives, etc. Computing device 210 includes one or more processors 216 that read data from various entities such as bus 212, memory 214 or I/O components 222. Presentation component(s) 218 present data indications to a person or other device. Exemplary presentation components 218 include a display device, speaker, printing component, vibrating component, etc. I/O ports 220 allow computing device 210 to be logically coupled to other devices including I/O components 222, some of which may be built in. Illustrative I/O components 222 include a microphone, joystick, game pad, satellite dish, scanner, printer, wireless device, etc.

Figure 16:
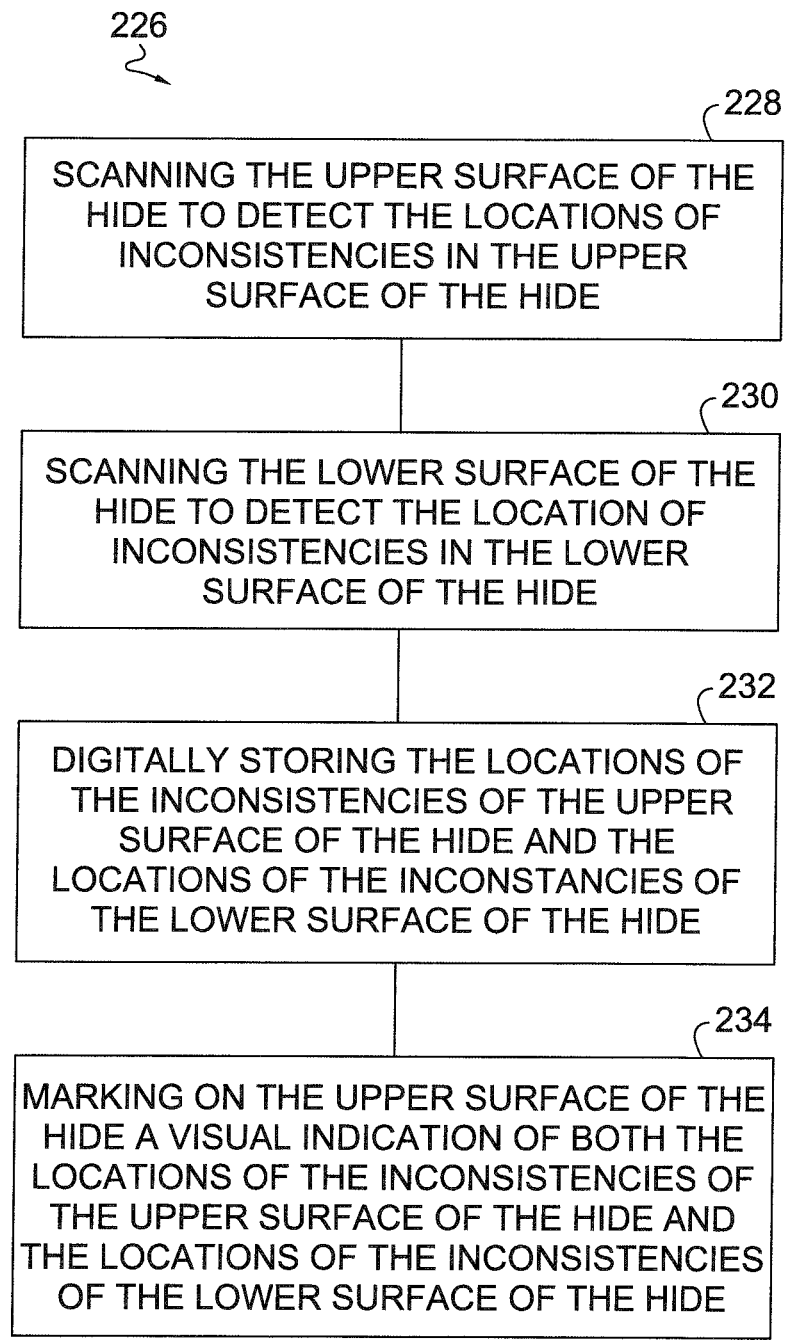
FIG. 16 depicts a flow diagram representing a method for detecting inconsistencies on both the upper and lower surfaces of a leather hide, in accordance with aspects hereof.

FIG. 16 depicts a method 226 for detecting inconsistencies on both upper and lower surfaces of a leather hide. A block 228 depicts the step of scanning the upper surface of the hide to detect the locations of inconsistencies in the upper surface of the hide. A block 230 depicts the step of scanning the lower surface of the hide to detect the locations of inconsistencies in the lower surface of the hide. A block 232 depicts the step of digitally storing the locations of the inconsistencies of the upper surface of the hide and the locations of the inconsistencies of the lower surface of the hide. A block 234 depicts the step of marking on the upper surface of the hide a visual indication of both the locations of the inconsistencies of the upper surface of the hide and the locations of the inconsistencies of the lower surface of the hide. Other steps can include moving the first camera assembly and the second camera assembly around the hide. The camera assemblies can be moved from edge to edge of the hide back and forth, as described herein. Still further steps can include providing at least one of the first camera assembly and the second camera assembly, a first camera for use with direct lighting and a second camera for use with indirect lighting and alternating scanning between the first camera and the second camera.

From the foregoing, it will be seen that this invention is one well adapted to attain all the ends and objects hereinabove set forth together with other advantages which are obvious and which are inherent to the structure.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

While specific elements and steps are discussed in connection to one another, it is understood that any element and/or steps provided herein is contemplated as being combinable with any other elements and/or steps regardless of explicit provision of the same while still being within the scope provided herein. Since many possible embodiments may be made of the disclosure without departing from the scope thereof, it is to be understood that all matter herein set forth or shown in the accompanying drawings is to be interpreted as illustrative and not in a limiting sense.

The invention claimed is:

1. A leather inspection apparatus for detecting inconsistencies on a surface of a leather hide, comprising:
   a frame capable of supporting the leather hide;
   a camera assembly comprising a first camera, the camera assembly movably coupled to the frame and capable of movement along a surface of the leather hide;
   a computing device comprising a processor and memory, the computing device is operatively coupled to the camera assembly; wherein the camera assembly detects locations of inconsistencies in an upper surface of the leather hide, wherein the computing device digitally stores the locations of the inconsistencies of the upper surface of the leather hide, and wherein the first camera detects inconsistencies based on direct lighting.

2. The leather inspection apparatus of claim 1, wherein the leather inspection apparatus further comprises a direct lighting source comprising a light source that provides direct lighting to the leather hide.

3. The leather inspection apparatus of claim 2, wherein the leather inspection apparatus further comprises an indirect lighting source comprising a light source that provides indirect lighting to the leather hide.

4. The leather inspection apparatus of claim 3, wherein the leather inspection apparatus further comprises a second camera for detecting inconsistencies based on the indirect lighting.

5. The leather inspection apparatus of claim 4, wherein the leather inspection apparatus alternates actuation between the first camera and the second camera to prevent light pollution between the first camera and the second camera.

6. The leather inspection apparatus of claim 5 further including a conveyor mechanism comprising a pair of rollers, the conveyor mechanism coupled to the frame and for moving the leather hide between the first camera and the second camera; wherein the conveyor mechanism is operatively coupled to the computing device so that the computing device controls the first camera, the second camera and the conveyor mechanism to effectuate a scan of multiple portions of the leather hide.

7. The leather inspection apparatus of claim 4, wherein the first camera and the second camera are each slidably mounted to the frame; wherein the first camera can scan the upper surface of the leather hide in a linear direction and the second camera can scan a lower surface of the leather hide in a linear direction.

8. The leather inspection apparatus of claim 1, wherein the leather inspection apparatus further comprises a pen capable of providing different types of visual indications on the upper surface of the leather hide.

9. The leather inspection apparatus of claim 8, wherein each different type of visual indication indicates a type of defect in the leather hide.

10. The leather inspection apparatus of claim 1, wherein the first camera includes a coaxial direct light source aligned with an axis of the first camera.

11. The leather inspection apparatus of claim 10, wherein the first camera with coaxial light source is actuated by the computing device as the first camera moves relative to the leather hide.

12. A leather inspection apparatus for detecting inconsistencies on a surface of a leather hide, comprising:
a frame capable of supporting the leather hide;
a first camera coupled to the frame; and
a computing device having a processor and memory, the computing device operatively coupled to the first camera; wherein the first camera detects locations of inconsistencies in the upper surface of the leather hide, wherein the computing device digitally stores the locations of the inconsistencies of the upper surface of the leather hide, and wherein the first camera detects inconsistencies based on direct lighting.

13. The leather inspection apparatus of claim 12, wherein the leather inspection apparatus further comprises a direct lighting source having a light source that provides direct lighting to the leather hide.

14. The leather inspection apparatus of claim 13, wherein the leather inspection apparatus further comprises an indirect lighting source having a light source that provides indirect lighting to the leather hide.

15. The leather inspection apparatus of claim 14, wherein the leather inspection apparatus further comprises a second camera for detecting inconsistencies based on the indirect lighting.

16. The leather inspection apparatus of claim 13 including a marking carriage movably coupled to the frame and operatively coupled to the computing device; wherein the marking carriage provides on the surface of the leather hide a visual indication of the locations of the inconsistencies.

17. A method for detecting inconsistencies on both an upper surface and a lower surface of a leather hide, comprising:
using a first camera to scan the leather hide to detect locations of inconsistencies in the upper surface of the leather hide; and
digitally storing the locations of the inconsistencies of the upper surface of the leather hide by way of a computing device.

18. The method of claim 17 further comprising:
marking on the upper surface of the leather hide a visual indication of the locations of the inconsistencies.

19. The method of claim 18 further comprising;
moving the first camera to detect the locations of inconsistencies in the lower surface of the leather hide.

20. The method of claim 17 further comprising;
providing at least one of a first camera assembly and a second camera assembly, a first camera for use with direct lighting and a second camera for use with indirect lighting; and alternating scanning between the first camera and the second camera.

\* \* \* \* \*